(12) United States Patent
Donitzky et al.

(10) Patent No.: US 9,877,869 B2
(45) Date of Patent: Jan. 30, 2018

(54) DEVICE AND PROCESS FOR MACHINING THE CORNEA OF A HUMAN EYE WITH FOCUSED PULSED LASER RADIATION

(71) Applicant: WaveLight GmbH, Erlangen (DE)

(72) Inventors: Christof Donitzky, Eckental (DE); Mathias Woelfel, Erlangen (DE); Johannes Krause, Stein (DE)

(73) Assignee: Wavelight GmbH (DE)

( * ) Notice: Subject to any disclaimer, the term of this patent is extended or adjusted under 35 U.S.C. 154(b) by 122 days.

(21) Appl. No.: 14/793,845

(22) Filed: Jul. 8, 2015

(65) Prior Publication Data

US 2015/0305941 A1    Oct. 29, 2015

Related U.S. Application Data

(63) Continuation of application No. 12/965,370, filed on Dec. 10, 2010, now abandoned.

(51) Int. Cl.
*A61F 9/008* (2006.01)
*A61F 9/009* (2006.01)

(52) U.S. Cl.
CPC ...... *A61F 9/00825* (2013.01); *A61F 9/00831* (2013.01); *A61F 9/009* (2013.01); *A61F 2009/0087* (2013.01); *A61F 2009/00872* (2013.01)

(58) Field of Classification Search
CPC .... A61F 9/008; A61F 9/00825–9/0084; A61F 2009/00872; A61F 2/143; A61F 2/146
USPC .......................................................... 606/4–6
See application file for complete search history.

(56) References Cited

U.S. PATENT DOCUMENTS

| | | | | |
|---|---|---|---|---|
| 2002/0173779 A1* | 11/2002 | Donitzky | ............... | A61F 9/008 606/5 |
| 2006/0100612 A1* | 5/2006 | van der Heyd | ......... | A61F 2/142 606/4 |
| 2008/0058777 A1* | 3/2008 | Kurtz | ..................... | A61F 9/008 606/4 |
| 2008/0058841 A1* | 3/2008 | Kurtz | ..................... | A61F 9/008 606/166 |

(Continued)

FOREIGN PATENT DOCUMENTS

| | | |
|---|---|---|
| RU | 2361553 C2 | 7/2009 |
| WO | 2008112292 A1 | 9/2008 |
| WO | 2009/039302 A2 | 3/2009 |

*Primary Examiner* — Nathan J Jenness
(74) *Attorney, Agent, or Firm* — Keiko Ichiye, Esq.

(57) ABSTRACT

A device for generating at least one continuous slit-like incision (42) from the posterior surface (48) as far as the anterior surface (46) of the cornea (44) of an eye, comprising a laser device for generating at least one part of the incision with focused pulsed laser radiation, the laser device including controllable components for setting the location of the focus, a control computer for controlling these components, and also a control program for the control computer. The control program contains instructions that are designed to bring about, upon execution by the control computer, the generation of at least one part of the incision (42) originating from the posterior surface (48) of the cornea, the cross-sectional contour of the incision—when observed in the direction from the anterior surface to the posterior surface—deviating from a straight line (60) perpendicular to the surface of the eye.

8 Claims, 2 Drawing Sheets

(56) References Cited

U.S. PATENT DOCUMENTS

| | | | |
|---|---|---|---|
| 2008/0114386 A1* | 5/2008 | Iliakis | A61F 2/142 606/166 |
| 2009/0137993 A1* | 5/2009 | Kurtz | A61F 9/00736 606/6 |
| 2011/0040293 A1* | 2/2011 | Bor | A61F 9/008 606/5 |
| 2011/0160710 A1* | 6/2011 | Frey | A61F 9/00825 606/6 |

* cited by examiner

DEVICE AND PROCESS FOR MACHINING THE CORNEA OF A HUMAN EYE WITH FOCUSED PULSED LASER RADIATION

CROSS REFERENCE TO RELATED APPLICATION

This application is a continuation of U.S. patent application Ser. No. 12/965,370, titled "DEVICE AND PROCESS FOR MACHINING THE CORNEA OF A HUMAN EYE WITH FOCUSED PULSED LASER RADIATION", filed 10 Dec. 2010.

TECHNICAL FIELD

The present invention is related to the generation of incisions in the human cornea by means of focused pulsed laser radiation. More particularly, the present invention relates to methods and systems for making incisions to create a passageway through the cornea.

BACKGROUND

For the generation of incisions by means of focused laser radiation in transparent material (transparent to the laser radiation), so-called laser-induced optical breakthrough), is utilised by way of physical effect. This results in a local vaporisation of the irradiated material, which is designated as photodisruption. The photodisruption is spatially restricted substantially to the area of the focus. By a plurality of such photodisruptions being placed side by side, the most diverse incision figures can be generated.

The photodisruptive generation of incisions in the human cornea by means of ultra-short-pulse focused laser radiation (with pulse durations within the femtosecond range) is known as such in the state of the art. For example, this technique of incision generation has been proposed many times for the preparation of the flap in the course of a LASIK operation (LASIK: laser in-situ keratomileusis).

However, corneal incisions are necessary not only in LASIK operations, but in a whole series of other forms of surgery. Intracorneal lenticle extraction can be mentioned as a relevant example, in which a lenticular piece of tissue in the cornea is separated out by means of two superjacent planar incisions touching one another at the margins.

SUMMARY

Within the scope of the invention are contemplated the creation of slit-like incisions that pass through from the anterior surface of a cornea to the posterior surface. Such incisions can open an access channel to the interior regions of an eye and are needed, for example, in operations on the human lens or in lamellar keratoplasties of the corneal endothelium, in order to be able to introduce and withdraw medical instruments and/or medical material (e.g. artificial replacement lens, donor tissue etc.).

The embodiments of the present invention provide a minimally invasive alternative to the mechanical generation of continuous incisions in the cornea by means of a scalpel.

Embodiments of the present invention provide a device for generating at least one continuous slit-like incision from the posterior surface of a cornea of an eye up to the anterior surface of the cornea, the device comprising a laser device for generating at least part of the incision with focused pulsed laser radiation, the laser device including controllable components for setting the location of the radiation focus, a control computer for controlling these components, and a control program for the control computer, the control program containing instructions that are designed to bring about, upon execution by the control computer, the generation of at least one part of the incision originating from the posterior surface of the cornea, at least this part of the incision exhibiting a cross-sectional contour—when viewed in the direction from the anterior surface to the posterior surface—that deviates from a straight line perpendicular to the surface of the eye. The laser radiation that is used preferentially has pulse durations within the range of less than 1 picosecond. The laser radiation wavelength can, for example, lie within the near-infrared region or within the ultraviolet region, so long as it permits a sufficient transmission deep into the cornea.

The term 'slit-like incision' is understood here to mean a two-dimensionally extended incision, the thickness of which is small, in particular vanishingly small in relation to the planar extent. For example, the thickness of the incision can correspond to only a single photodisruption, i.e. the photodisruptions are arranged side by side only in a single plane. The cross-sectional contour from anterior surface to posterior surface of the material being cut (e.g., a cornea) is to be understood as a contour in a longitudinal cross-section. The length of the incision is determined by the spacing from anterior surface to posterior surface of the cornea and by the chosen cross-sectional contour of the incision on this line segment. The incision opens up a slit-like access to the interior of the eye through the cornea, in which connection this slit, when observed in top view of the anterior surface of the cornea, can be substantially rectilinear or even more or less strongly curved. The length of the slit, viewed in such a top view (corresponding to the width of the incision), amounts, for example, to only a few millimeters. Said length can be established in a manner depending on the requirements of the concrete application, in particular in a manner depending on the size of the instruments and materials to be introduced or withdrawn through the slit. To the extent that several continuous incisions in the cornea are being prepared, at least a fractional number of these incisions can exhibit a mutually deviating cross-sectional contour from anterior surface to posterior surface of the cornea and/or a mutually deviating width. It will be understood that at least a fractional number of the incisions can equally well exhibit an identical cross-sectional contour and also an identical width.

To better ensure a good self-sealing of the cornea opened by the incision, it is advisable if the cross-sectional contour of the incision exhibits at least one sharp bend. In this case the cross-sectional contour of the incision can exhibit a substantially rectilinear portion on both sides of the sharp bend. As an alternative or in addition to a single or multiple kinking, the longitudinal cross-section of the incision can exhibit one or more arcuate or undulating segments. A good self-sealing of the cornea can also be obtained in this way.

For a particularly good self-sealing, the cross-sectional contour of the incision can exhibit several sharp bends. In this case it has proved to be advantageous if the cross-sectional contour of the incision exhibits at least one rectilinear portion extending between two sharp bends, which extends substantially perpendicular to the surface of the eye. Since the surface of the human eye is curved and for this reason the perpendicular at different points on the surface of the eye is orientated differently, whenever a particular orientation of the cross-sectional contour or of a part of the same to the perpendicular to the surface of the eye is under discussion a perpendicular at the point of the incision in question is always meant.

To the extent that the cross-sectional contour of the incision exhibits at least three rectilinear portions, a succession of these portions in the manner of a zigzag pattern is recommended.

With regard to the location of the incision in the eye, said incision can extend along or across an imaginary circular line that is substantially concentric with the pupil of the eye, i.e. its width extends in this direction. In this case the incision can, for example, be made to extend tangentially relative to the circular line, but it can also be made to extend at an arbitrary angle to the circular line. The imaginary circular line can lie inside or outside the pupillary margin (when observed in a top view of the eye along the pupillary axis), but in any case it lies inside the limbus of the eye. When observed in a cross-section in the width direction, the contour of the incision is expediently rectilinear.

The incision can be made with a substantially constant width over its length from the anterior surface to the posterior surface of the cornea. Alternatively it can have a width tapering towards the posterior surface, i.e. it can taper (e.g. steadily or in stepwise manner) towards the posterior surface. The incision width can also be made to increase towards the posterior surface.

To the extent that there is a demand for the preparation of a plurality of incisions, the instructions of the control program can be set to bring about the generation, in each instance, of at least one part of several incisions. Of these, at least a fractional number of at least two incisions can be arranged distributed along an imaginary circular line that is substantially concentric with the pupil of the eye. Generally, the incisions can be arranged distributed over several imaginary circular lines that are substantially concentric with the pupil of the eye. The centring of the aforementioned circular lines in relation to the pupillary midpoint relates here to a viewing mode in top view of the eye along the pupillary axis of the eye, in which connection it will be understood that in a modification the circular lines mentioned here can also be situated eccentrically relative to the pupillary midpoint.

In one embodiment of the present invention the at least one incision can be totally generated with the laser device, that is to say, in this embodiment the instructions of the control program can be designed to generate, upon execution by the control computer, the incision over its entire continuous length from the posterior surface as far as the anterior surface of the cornea. In an alternative embodiment the laser device can be programmed in such a way that it generates only a part of the incision originating from the posterior surface of the cornea but terminating at a distance from the anterior surface of the cornea. For example, this part of the incision generated by laser technology terminates at most about 100 µm, better at most about 70 µm, beneath the anterior surface of the cornea. For example, the incision portion can terminate about 50 µm beneath the anterior surface of the cornea, that is to say, at the point up to which the corneal epithelium extends.

It is further contemplated by the embodiments of the present invention that the part of the incision generated by laser technology can terminate at a still shorter distance from the anterior surface of the cornea, about only 20 µm or 30 µm. In each case the remaining part of the cornea is preferentially thinner than that part of the cornea which has been penetrated by the part of the incision generated by laser technology. Subsequent to the generation of the incision by laser technology this remaining part can be severed by the operating surgeon with a conventional mechanical cutting instrument (scalpel). This enables a method of treatment in which the part of the incision to be generated by laser technology is firstly generated in a non-sterile environment without this harbouring particular risks for the patient, because in this non-sterile environment the eye is still not opened up completely. The completion of the incision by manual severing of the remaining residual portion of the cornea can then be performed by the operating surgeon in a sterile environment in which the actual operation for which the access channel in the eye is needed is also carried out. In such an embodiment, the device according to the invention can comprise, in addition to the laser device, at least one scalpel with which the operating surgeon can complete the incision as far as the anterior surface of the cornea.

BRIEF DESCRIPTION OF THE DRAWINGS

The invention will be elucidated further in the following on the basis of the appended drawings.

DETAILED DESCRIPTION

Figure 1:
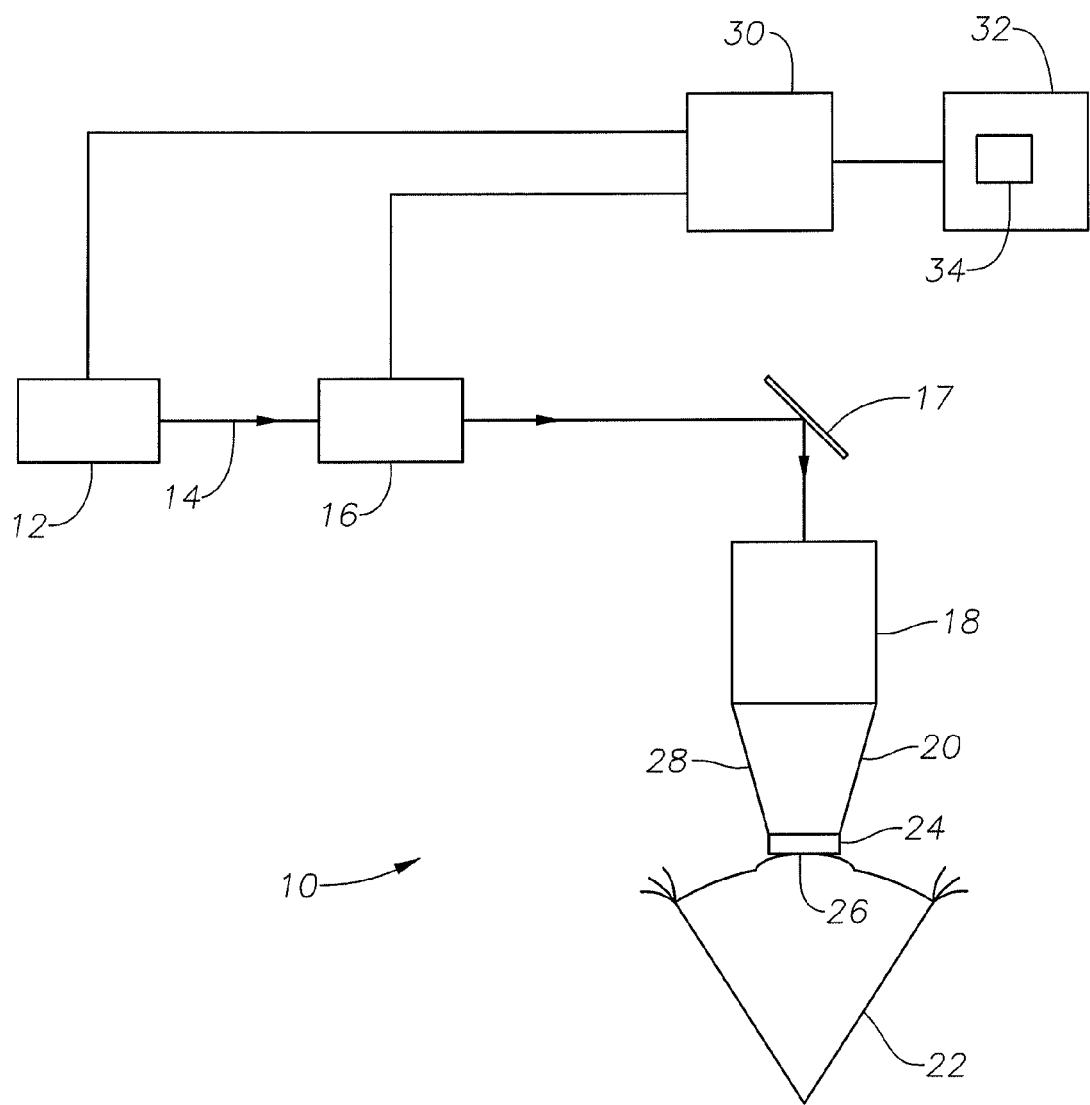
FIG. 1 in schematic block representation, an exemplary embodiment of a laser device for placing continuous incisions in the human cornea in accordance with the teachings of the invention, FIG. 2 schematically, an exemplary arrangement pattern for several continuous corneal incisions, FIG. 3 schematically, an exemplary corneal incision when observed in an x-z cross-section through the cornea, and FIG. 4 the incision shown in FIG. 3 when observed in a y-z cross-section through the cornea.

Reference will firstly be made to FIG. 1. The laser device therein, generally denoted by 10, includes a laser-source 12 which generates a laser beam 14 with pulse durations within the femtosecond range. In the beam path of the laser beam 14 a number of components are arranged, inter alia a scanner 16 indicated here schematically as a unified functional block, an immovable deviating mirror 17 and also a focusing objective 18. The scanner 16 serves for transverse and longitudinal control of the location of the focal point of the laser beam 14. 'Transverse' here designates a direction at right angles to the direction of propagation of the laser beam 14 in the region of the eye; 'longitudinal' corresponds to the direction of beam propagation. In conventional notation the transverse plane is designated as the x-y plane, whereas the longitudinal direction is designated as the z-direction. A corresponding x-y-z coordinate frame has been drawn in FIG. 1 for purposes of illustration.

For the purpose of transverse deflection of the laser beam 14 (i.e. in the x-y plane) the scanner 16 can, for example, include a pair of galavanometrically actuated scanner mirrors which are arranged so as to be capable of being tilted about mutually perpendicular axes. Alternatively, for example, a transverse deflection by means of an electro-optical crystal cab be used. For the z-control of the focal position, the scanner 16 can, for example, contain a longitudinally adjustable lens or a lens of variable refractive power or a deformable mirror, with which the divergence of the laser beam 14 and consequently the z-position of the beam focus can be influenced, with the focusing setting of the focusing objective 18 unchanged.

It will be understood that the components of the scanner 16 serving for the transverse focus control and for the longitudinal focus control can be arranged distributed along the beam path of the laser beam 14 and, in particular, apportioned to different modular units. For example, the function of the z-focus adjustment can be fulfilled by a lens arranged in a beam expander (e.g. Galilean telescope), whereas the components serving for the transverse focus control can be accommodated in a separate modular unit between the beam expander and the focusing objective 18. The representation of the scanner 16 as a unified functional block in FIG. 1 serves merely for better clarity of layout.

The focusing objective 18 can be an f-theta objective and is desirably separably coupled on its beam-emergence side with a patient adapter 20 which forms an abutment interface for the cornea of an eye 22 to be treated. For this purpose the patient adapter 20 can comprise a contact element 24 which is transparent to the laser radiation and which on its underside facing towards the eye forms an abutment face 26 for the cornea. In the exemplary case shown, the abutment face 26 is constructed as a plane face and serves for levelling the cornea, by the contact element 24 being pressed against the eye 22 with appropriate pressure or by the cornea being aspirated onto the contact face 26 by reduced pressure.

The contact element 24 (in the case of plane-parallel construction, ordinarily designated as an applanation plate) is attached at the narrower end of a conically widening carrier sleeve 28. The connection between the contact element 24 and the carrier sleeve 28 can be inseparable, for example by virtue of adhesion bonding; alternatively it can be separable, for instance by virtue of a screw joint. The carrier sleeve 28 possesses at its wider sleeve end, in a manner not represented in any detail, suitable coupling structures for the purpose of coupling to the focusing objective 18.

The laser-source 12 and the scanner 16 are controlled by a control computer 30 which operates in accordance with a control program 34 stored in a memory 32. The control program 34 contains instructions (program code) that bring about, upon execution by the control computer 30, such a control of the location of the beam focus of the laser beam 14 that one or more continuous, slit-like incisions can be generated in the cornea of the eye 22 bearing against the contact element 24.

Figure 2:
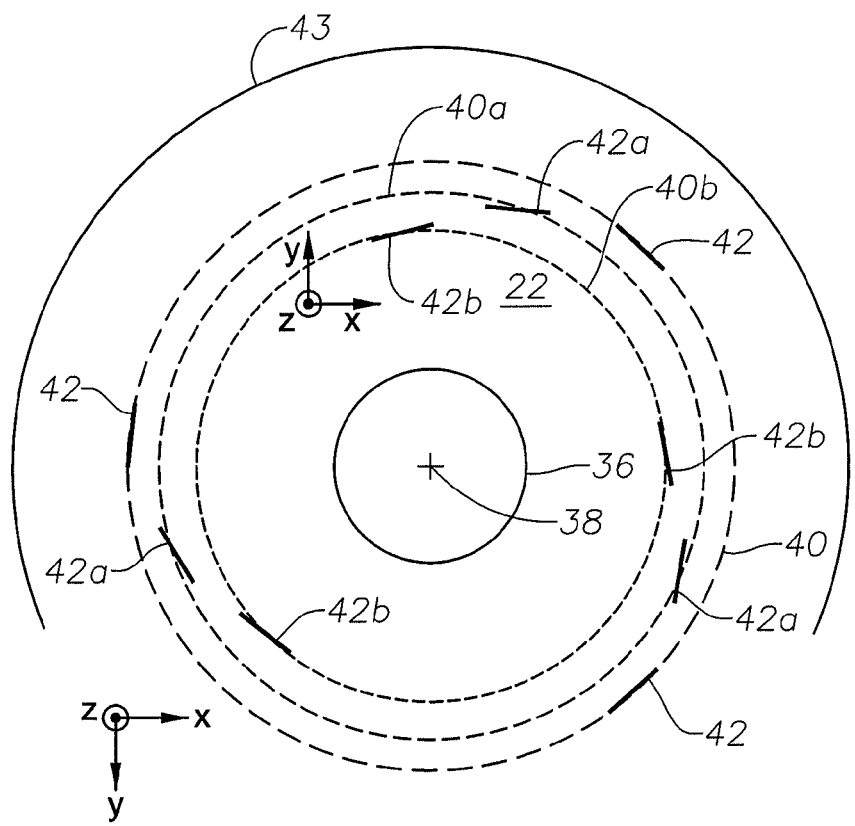

A possible arrangement pattern of these incisions is shown schematically in FIG. 2. A pupil 36 is indicated therein by its pupillary margin. The pupil 36 possesses a pupillary centre 38. Concentrically with the pupillary centre 38 there is drawn in dashed manner an imaginary circular line 40 which surrounds the pupil 36 externally at a radial spacing. Along this circular line 40, distributed at substantially identical spacings, three slit incisions 42 have been drawn in, which penetrate the cornea of the eye 22 over the entire thickness thereof and each open up an access channel to the anterior chamber of the eye and to the remaining inner regions of the eye. It will be discerned that in the exemplary case shown in FIG. 2 the incisions 42 possess approximately identical widths and have been executed rectilinearly in the direction of their width. In this case they are situated approximately tangentially relative to the circular line 40. It will be understood that at least a fractional number of the incisions 42 can alternatively be oriented across (at an arbitrary angle to) the circular line 40.

It will be understood, furthermore, that the number of incisions 42 can be variable. Depending on the operation to be carried out, a single incision 42 can suffice, or several incisions 42 may be necessary. It is also not necessary to arrange all the incisions 42 distributed along the same circular line 40. It is contemplated to be within the scope of the invention to place at least a fractional number of the incisions at a different radial spacing from the pupillary centre 38. This can, for example, be obtained by an eccentric location of the circular line 40 in relation to the pupillary centre 38. Alternatively, it can be obtained by the incisions being distributed over several centrically arranged circular lines, as illustrated in exemplary manner in FIG. 2 on the basis of the additional circular lines 40a, 40b drawn in dashed manner and the further incisions 42a, 42b. The limbus of the eye is sketched schematically in this Figure by 43. Incidentally, it is also not necessary to distribute the incisions along a circular path.

Overall, with respect to the distribution in the radial direction and also with respect to the distribution in the peripheral direction there is, in principle, no restriction for the arrangement pattern of the incisions 42.

The incisions 42 can be configured identically or differently. For a possible configuration of one of the incisions, reference will now be made to FIGS. 3 and 4. These show transverse views of the same incision from different viewing directions, as illustrated by the xyz coordinate frames which have been drawn in.

Figure 3:
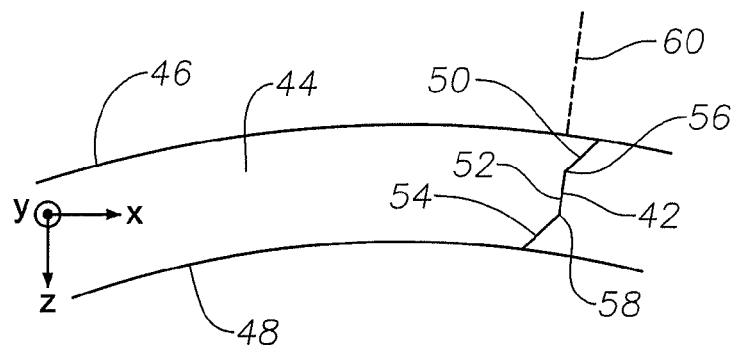
Figure 4:
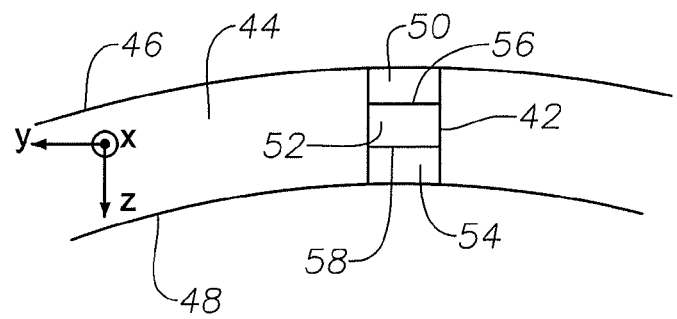

The cornea of the eye to be treated is denoted by 44 in FIGS. 3 and 4. It possesses an anterior surface 46 and also a posterior surface 48. In both Figures it is shown in a relaxed, non-applanated state (i.e. after removal from the contact element 24).

The exemplary incision 42 shown in FIGS. 3 and 4 displays, in a transverse view from the narrow slit side, a zigzag pattern extending from the anterior surface 46 to the posterior surface 48 with several (here, three) rectilinear portions 50, 52, 54 which are separated pairwise in each instance by a sharp bend 56, 58. The middle portion 52 extends substantially parallel to a normal 60 to the surface of the eye which has been drawn in dashed manner (the surface of the eye is synonymous here with the anterior surface 46 of the cornea). It will be understood that this observation only holds for a normal to the surface in the region of the incision 42, since in other regions of the anterior surface of the eye the respective normal to the surface is oriented spatially differently from the normal 60 which has been drawn in.

Instead of the zigzag or sawtooth pattern shown in FIG. 3, it is readily possible to execute the incision 42 with an undulatory profile. The sharp bends 56, 58 can then be replaced by roundish arcs.

The transverse view of the incision 42 from the broad slit side according to FIG. 4 illustrates in addition that in the exemplary case shown the incision 42 possesses substantially constant width over its entire length (whereby here alternatively a taper towards the posterior surface 48 can also be made). For the generation of the incision 42, the focus of the laser beam that is used is moved in a linear grid in successive scan lines, whereby for the purpose of avoiding possible shielding effects the generation of the incision is expediently begun on the posterior surface 48 of the cornea 44. From there, the individual scan lines progress increasingly in the direction towards the anterior surface 46. The lines drawn in bold type in FIG. 4 and extending within the slit width illustrate the line scan for the beam focus in the course of generation of the incision 42.

Although embodiments of the proposed device, system and method of the present invention have been illustrated in the accompanying drawings and described in the description, it will be understood that the invention is not limited to the embodiments disclosed herein. In particular, the proposed technique is capable of numerous rearrangements, modifications and substitutions without departing from the scope of the invention as set forth and defined by the following claims.

The invention claimed is:

1. A method for generating at least one incision in a cornea of a human eye, the method comprising:

generating, with laser radiation from a laser device, a slit-like incision from a posterior surface to an anterior surface of the cornea, the incision forming a slit in an x-y plane in the cornea, the slit in the x-y plane being substantially rectilinear and arranged along a circular line substantially concentric with the pupil of the eye, a width of the slit in the x-y plane being a few millimeters sized to introduce a medical instrument; and generating, with the laser radiation from by the laser device, the slit-like incision with a cross-sectional contour in an x-z cross-section, the cross-sectional contour comprising a posterior portion, a middle portion connected to the posterior portion, and an anterior portion connected to the middle portion, the posterior portion angled from the middle portion towards the pupillary center, the middle portion substantially perpendicular to the surface of the eye, and the anterior portion angled from the middle portion away from the pupillary center, wherein the posterior portion, the middle portion, and the anterior portion are substantially rectilinear.

2. The method according to claim 1, wherein the cross-sectional contour of the incision exhibits at least one bend.

3. The method according to claim 1, wherein the width of the slit is substantially constant from the posterior surface to the anterior surface.

4. The method according to claim 1, wherein the width of the slit increases from the posterior surface to the anterior surface.

5. The method according to claim 1, wherein the width of the slit decreases from the posterior surface to the anterior surface.

6. The method according to claim 1, further comprising:
generating, with the laser radiation from the laser device, an additional slit-like incision with a slit arranged along the circular line.

7. The method according to claim 1, further comprising:
generating, with the laser radiation from the laser device, an additional slit-like incision with a slit arranged along another circular line substantially concentric with the pupil of the eye.

8. The method according to claim 1, wherein the laser radiation possesses pulse durations of less than 1 picosecond.

* * * * *